United States Patent
Daniel et al.

(10) Patent No.: US 9,790,304 B2
(45) Date of Patent: Oct. 17, 2017

(54) PROCESS FOR PRODUCING WATER-ABSORBENT POLYMER PARTICLES BY POLYMERIZING DROPLETS OF A MONOMER SOLUTION

(71) Applicant: BASF SE, Ludwigshafen (DE)

(72) Inventors: Thomas Daniel, Waldsee (DE);
Norbert Herfert, Altenstadt (DE);
Stephan Bauer, Hochheim (DE);
Katrin Baumann, Mannheim (DE);
Birgit Reinhard, Limburgerhof (DE);
Jürgen Freiberg, Lampertheim (DE);
Rudolf Schliwa, Alzenau (DE)

(73) Assignee: BASF SE, Ludwigshafen (DE)

( * ) Notice: Subject to any disclaimer, the term of this patent is extended or adjusted under 35 U.S.C. 154(b) by 135 days.

(21) Appl. No.: 14/442,501

(22) PCT Filed: Nov. 11, 2013

(86) PCT No.: PCT/EP2013/073457
§ 371 (c)(1),
(2) Date: May 13, 2015

(87) PCT Pub. No.: WO2014/079710
PCT Pub. Date: May 30, 2014

(65) Prior Publication Data
US 2016/0272745 A1    Sep. 22, 2016

Related U.S. Application Data

(60) Provisional application No. 61/728,845, filed on Nov. 21, 2012.

(30) Foreign Application Priority Data

Nov. 21, 2012 (EP) .................................... 12193669

(51) Int. Cl.
| | | |
|---|---|---|
| *B01J 20/32* | (2006.01) | |
| *C08F 220/06* | (2006.01) | |
| *C08F 6/00* | (2006.01) | |
| *A61L 15/42* | (2006.01) | |
| *A61L 15/60* | (2006.01) | |
| *A61L 15/22* | (2006.01) | |
| *C08L 33/02* | (2006.01) | |
| *A61L 15/24* | (2006.01) | |
| *B01J 20/26* | (2006.01) | |
| *B01J 20/28* | (2006.01) | |

(52) U.S. Cl.
CPC ............ *C08F 220/06* (2013.01); *A61L 15/22* (2013.01); *A61L 15/24* (2013.01); *A61L 15/42* (2013.01); *A61L 15/60* (2013.01); *B01J 20/267* (2013.01); *B01J 20/2805* (2013.01); *B01J 20/28023* (2013.01); *C08F 6/005* (2013.01); *C08L 33/02* (2013.01)

(58) Field of Classification Search
CPC ................................ B01J 20/32; B01J 20/26
USPC ......................................................... 502/402
See application file for complete search history.

(56) References Cited

U.S. PATENT DOCUMENTS

| 5,269,980 A | 12/1993 | Levendis et al. |
| 2010/0029866 A1 | 2/2010 | Losch et al. |
| 2011/0059329 A1 | 3/2011 | Dobrawa et al. |
| 2011/0237754 A1 | 9/2011 | Daniel et al. |
| 2011/0238026 A1 | 9/2011 | Zhang et al. |
| 2012/0141792 A1 | 6/2012 | Stueven et al. |

FOREIGN PATENT DOCUMENTS

| EP | 0 348 180 A2 | 12/1989 |
| WO | WO-96/40427 A1 | 12/1996 |
| WO | WO-2008/009580 A1 | 1/2008 |
| WO | WO-2008/052971 A1 | 5/2008 |
| WO | WO-2011/026876 A1 | 3/2011 |
| WO | WO-2011/113728 A1 | 9/2011 |
| WO | WO-2011/117263 A1 | 9/2011 |
| WO | WO-2013/045163 A1 | 4/2013 |

OTHER PUBLICATIONS

Buchholz, Fredric L., et al. *Modern Superabsorbent Polymer Technology*, "Commercial Processes for the Manufacture of Superabsorbent Polymers." New York: John Wiley & Sons, Inc., 1998, pp. 71-103.
International Search Report for international application No. PCT/EP2013/073457, dated Feb. 12, 2014.

*Primary Examiner* — Edward Johnson
(74) *Attorney, Agent, or Firm* — Marshall, Gerstein & Borun LLP

(57) ABSTRACT

The present invention relates to a process for producing water-absorbent polymer particles by polymerizing droplets of a monomer solution comprising less than 0.3% by weight of persulfate and at least 0.05% by weight of azo initiator and thermal aftertreatment of the formed polymer particles at less than 100° C. in a fluidized bed for 60 to 300 minutes.

14 Claims, 8 Drawing Sheets

Figure 1:
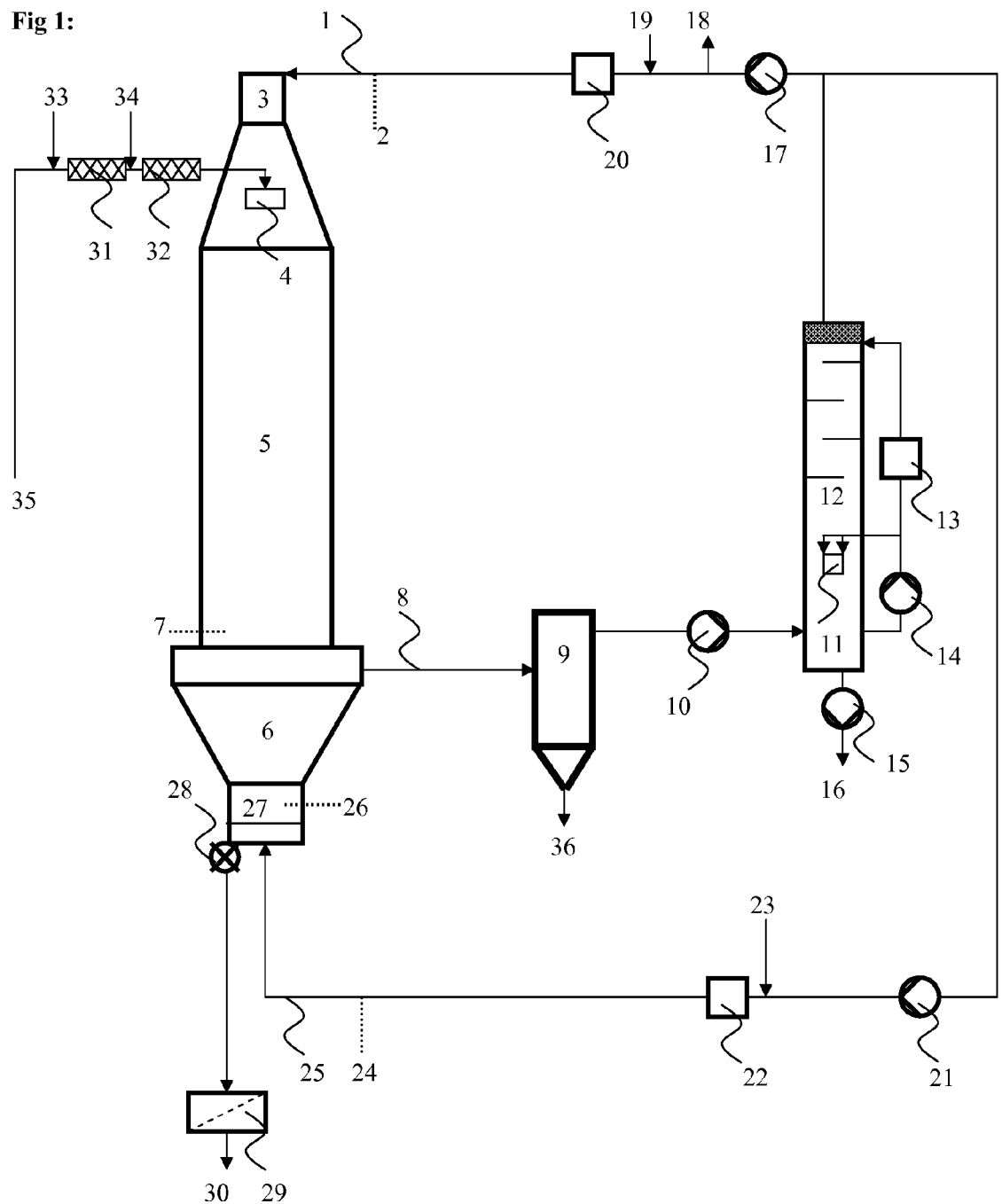
Figure 2:
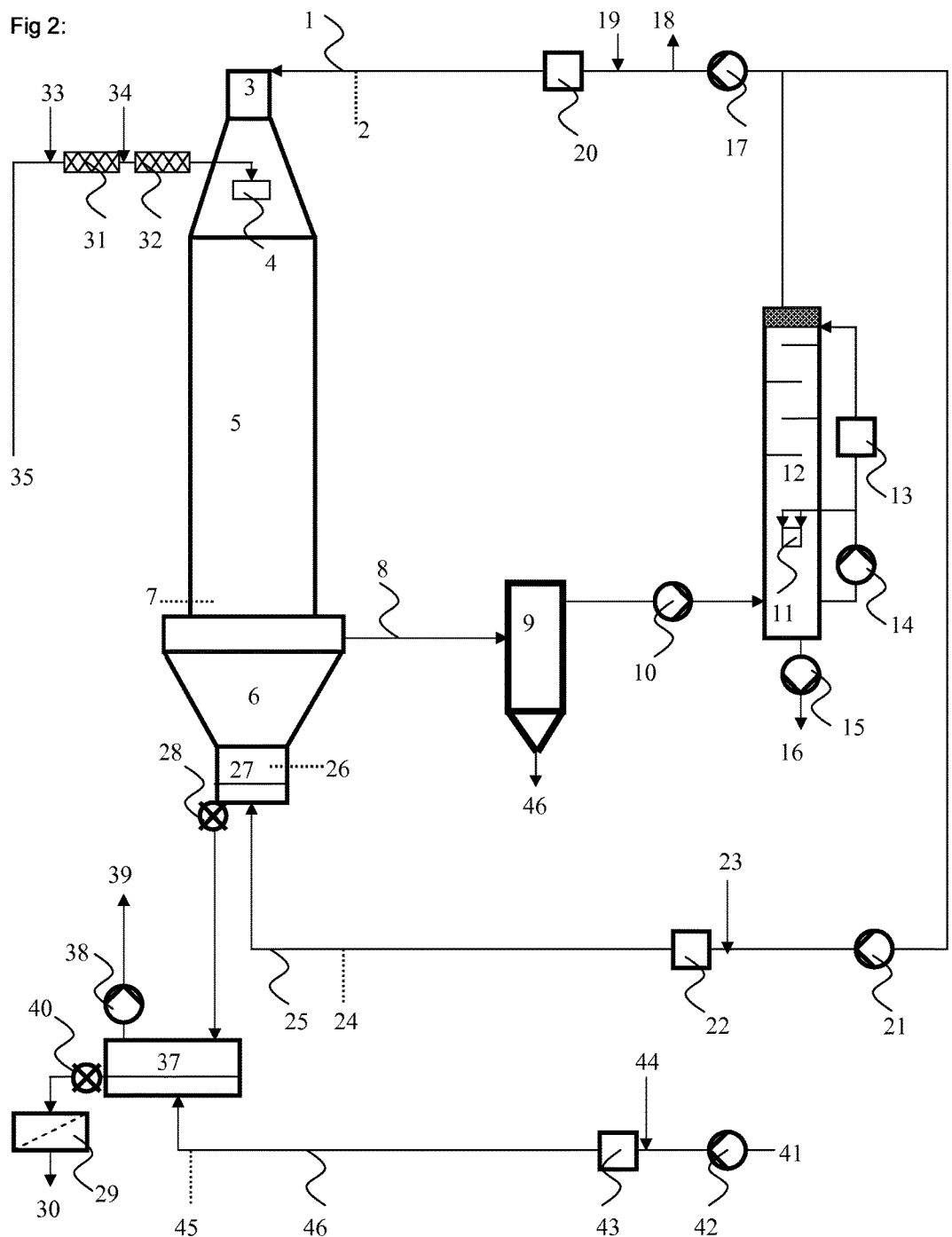

PROCESS FOR PRODUCING WATER-ABSORBENT POLYMER PARTICLES BY POLYMERIZING DROPLETS OF A MONOMER SOLUTION

CROSS-REFERENCE TO RELATED APPLICATIONS

This is the U.S. National Stage of PCT/EP2013/073457, filed Nov. 11, 2013, which claims the benefit of EP Patent Application No. 12193669.4, filed Nov. 21, 2012, and U.S. Provisional Patent Application No. 61/728, 845, filed Nov. 21, 2012, incorporated herein by reference in its entirety.

DESCRIPTION

The present invention relates to a process for producing water-absorbent polymer particles by polymerizing droplets of a monomer solution comprising less than 0.3% by weight of persulfate and at least 0.05% by weight of azo initiator and thermal aftertreatment of the formed polymer particles at less than 100° C. in a fluidized bed for 60 to 300 minutes.

The preparation of water-absorbent polymer particles is described in the monograph "Modern Superabsorbent Polymer Technology", F. L. Buchholz and A. T. Graham, Wiley-VCH, 1998, on pages 71 to 103.

Being products which absorb aqueous solutions, water-absorbent polymer particles are used to produce diapers, tampons, sanitary napkins and other hygiene articles, but also as water-retaining agents in market gardening. Water-absorbent polymer particles are also referred to as "super-absorbent polymers" or "superabsorbents".

The preparation of water-absorbent polymer particles by polymerizing droplets of a monomer solution is described, for example, in EP 0 348 180 A1, WO 96/40427 A1, U.S. Pat. No. 5,269,980, WO 2008/009580 A1, WO 2008/052971 A1, WO2011/026876 A1, and WO 2011/117263 A1.

Polymerization of monomer solution droplets in a gas phase surrounding the droplets ("dropletization polymerization") affords round water-absorbent polymer particles of high mean sphericity (mSPHT). The mean sphericity is a measure of the roundness of the polymer particles and can be determined, for example, with the Camsizer® image analysis system (Retsch Technology GmbH; Haan; Germany).

It was an object of the present invention to provide water-absorbent polymer particles having improved properties, i.e. water-absorbent polymer particles having a high bulk density, a high centrifuge retention capacity (CRC), a high absorption under a load of 21.0 g/cm² (AUL), a low level of residual monomers and an improved whiteness.

The object is achieved by a process for producing water-absorbent polymer by polymerizing droplets of a monomer solution comprising less than 0.3% by weight of persulfate and at least 0.05% by weight of azo initiator in a surrounding heated gas phase in a reaction zone and thermal posttreatment in a fluidized bed, wherein the temperature of the gas leaving the reaction zone is less than 150° C., the temperature of the water-absorbent polymer particles during the thermal posttreatment is less than 100° C. and the residence time of the water-absorbent polymer particles in the fluidized bed is from 60 to 300 minutes.

The present invention is based on the finding that the temperature the water-absorbent polymer particles in the fluidized bed has a strong impact on the bulk density, the level of residual monomers and the absorption under a load of 21.0 g/cm² (AUL). On increasing the temperature there is a significant decrease of these values. For getting water-absorbent polymer particles having a high bulk density, a low level of residual monomers and a high absorption under a load of 21.0 g/cm² (AUL) it is advantageous reducing the temperature and prolonging the residence time in the internal fluidized bed. The reduction of the level of residual monomers can be accelerated by increasing the steam content of the gas to be used in the internal fluidized bed.

The present invention is further based on the finding that persulfates are necessary for a low level of residual monomers. Persulfates are also the reason for discoloration of the water-absorbent polymer particles. So, only small amounts of persulfates shall be used.

The present invention is further based on the finding that azo initiators have a strong impact on the centrifuge retention capacity (CRC). Persulfates do not have such impact.

The result of the specific conditions according to the process of the present invention are water-absorbent polymer particles having a high bulk density, a high centrifuge retention capacity (CRC), a high absorption under a load of 21.0 g/cm² (AUL), a low level of residual monomers and an improved whiteness.

The present invention further provides water-absorbent polymer particles having a bulk density of at least 0.65 g/cm³, a centrifuge retention capacity (CRC) at least 35 g/g and a HC value of at least 80.

The present invention further provides fluid-absorbent articles which comprise the inventive water-absorbent polymer particles.

DETAILED DESCRIPTION OF THE INVENTION

Preparation of the Water-Absorbent Polymer Particles

The water-absorbent polymer particles are prepared by a process, comprising the steps forming water-absorbent polymer particles by polymerizing a monomer solution, comprising a) at least one ethylenically unsaturated monomer which bears acid groups and may be at least partly neutralized,
b) at least one crosslinker,
$c_1$) less than 0.3% by weight, based on monomer a), of at least one persulfate,
$c_2$) at least 0.05% by weight, based on monomer a), of at least one azo initiator,
d) optionally one or more ethylenically unsaturated monomers copolymerizable with the monomers mentioned under a),
e) optionally one or more water-soluble polymers, and
f) water,
in a surrounding heated gas phase in a reaction zone and thermal posttreatment in a fluidized bed, wherein the temperature of the gas leaving the reaction zone is less than 150° C., the temperature of the water-absorbent polymer particles during the thermal posttreatment is less than 100° C. and the residence time of the water-absorbent polymer particles in the fluidized bed is from 60 to 300 minutes.

The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogen-carbonates and hydroxides of magnesium, calcium, strontium, zinc or aluminum as powders, slurries or solutions and mixtures of any of the above neutralization agents. Example for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tartrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid).

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, poly-ethyleneglycole diallylethers (based on polyethylene glycole having a molecular weight between 400 and 20000 g/mol), N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 18-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). On increasing the amount of crosslinker b) the centrifuge retention capacity (CRC) decreases and the absorption under a pressure of 21.0 g/cm$^2$ (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion. The initiators c) should be water-soluble.

Particularly preferred initiators c) are azo initiators such as 2,2"-azobis[2-(2-imidazolin-2-yl)propane]dihydrochloride, 2,2"-azobis(2-amidinopropane)dihydrochloride, 4,4"-azobis(4-cyanopentanoic acid), 4,4"-azobis(4-cyanopentanoic acid) sodium salt, 2,2"-azobis[2-methyl-N-(2-hydroxyethyl)-propionamide and 2,2"-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany). Of course it is also possible within the scope of the present invention to use the purified salts or acids of 2-hydroxy-2-sulfinatoacetic acid and 2-hydroxy-2-sulfonatoacetic acid—the latter being available as sodium salt under the trade name Blancolen® (Brüggemann Chemicals; Heilbronn; Germany).

The amount of persulfate $c_1$) to be used is less than 0.3% by weight, preferably from 0.01 to 0.25% by weight, more preferably from 0.05 to 0.2% by weight, most preferably from 0.1 to 0.15% by weight, each based on monomer a). If the amount of persulfate is too low, a sufficient low level of residual monomers cannot be achieved. If the amount of persulfate is too high, the water-absorbent polymer particles do not have a sufficient whiteness.

The amount of azo initiator $c_2$) to be used is at least 0.05% by weight, preferably from 0.1 to 2% by weight, more preferably from 0.15 to 1% by weight, most preferably from 0.2 to 0.5% by weight, each based on monomer a). If the amount of azo initiator is too low, a high centrifuge retention capacity (CRC) cannot be achieved. If the amount of azo initiator is too high, the process becomes too expensive.

Examples of ethylenically unsaturated monomers d) which are copolymerizable with the monomers a) are acrylamide, methacrylamide, hydroxyethyl acrylate, hydroxyethyl methacrylate, butanediol monoacrylate, butanediol monomethacrylate dimethylaminoethyl acrylate, dimethylaminoethyl methacrylate, dimethylaminopropyl acrylate and diethylaminopropyl methacrylate.

Useful water-soluble polymers e) include polyvinyl alcohol, modified polyvinyl alcohol comprising acidic side groups for example Poval® K (Kuraray Europe GmbH; Frankfurt; Germany), polyvinylpyrrolidone, starch, starch derivatives, modified cellulose such as methylcellulose, carboxymethylcellulose or hydroxyethylcellulose, gelatin, polyglycols or polyacrylic acids, polyesters and polyamides, polylactic acid, polyvinylamine, polyallylamine, water soluble copolymers of acrylic acid and maleic acid available as Sokalan® (BASF SE; Ludwigshafen; Germany), preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pa·s, more preferably from 0.004 to 0.015 Pa·s, most preferably from 0.005 to 0.01 Pa·s. The mean droplet diameter in the droplet generation rises with rising dynamic viscosity.

The monomer solution has, at 20° C., a density of preferably from 1 to 1.3 $g/cm^3$, more preferably from 1.05 to 1.25 $g/cm^3$, most preferably from 1.1 to 1.2 $g/cm^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension.

Polymerization

The water-absorbent polymer particles are produced by polymerizing droplets of the monomer in a surrounding heated gas phase, for example using a system described in WO 2008/040715 A2, WO 2008/052971 A1, WO 2008/069639 A1 and WO 2008/086976 A1.

The droplets are preferably generated by means of a droplet plate. A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

Within the scope of the present invention it is also possible to use two or more droplet plates with different bore diameters so that a range of desired particle sizes can be produced. It is preferable that each droplet plate carries only one bore diameter, however mixed bore diameters in one plate are also possible.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. In a preferred embodiment of the present invention the pressure drop is from 4 to 5 bar. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water.

The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water.

Useful coatings include for example fluorous polymers, such as perfluoroalkoxyethylene, polytetrafluoroethylene, ethylene-chlorotrifluoroethylene copolymers, ethylene-tetrafluoroethylene copolymers and fluorinated polyethylene.

The coatings can be applied to the substrate as a dispersion, in which case the solvent is subsequently evaporated off and the coating is heat treated. For polytetrafluoroethylene this is described for example in U.S. Pat. No. 3,243,321.

Further coating processes are to be found under the headword "Thin Films" in the electronic version of "Ullmann's Encyclopedia of Industrial Chemistry" (Updated Sixth Edition, 2000 Electronic Release).

The coatings can further be incorporated in a nickel layer in the course of a chemical nickelization.

It is the poor wettability of the droplet plate that leads to the production of monodisperse droplets of narrow droplet size distribution.

The droplet plate has preferably at least 5, more preferably at least 25, most preferably at least 50 and preferably up to 750, more preferably up to 500 bores, most preferably up to 250. The diameter of the bores is adjusted to the desired droplet size.

The separation of the bores is usually from 5 to 50 mm, preferably from 6 to 40 mm, more preferably from 7 to 30 mm, most preferably from 8 to 25 mm. Smaller separations of the bores may cause agglomeration of the polymerizing droplets.

The diameter of the bores is preferably from 50 to 500 µm, more preferably from 100 to 300 µm, most preferably from 150 to 250 µm.

For optimizing the average particle diameter, droplet plates with different bore diameters can be used. The variation can be done by different bores on one plate or by using different plates, where the each plate has a different bore diameter. The average particle size distribution can be monomodal, bimodal or multimodal. Most preferably it is monomodal or bimodal.

The temperature of the monomer solution as it passes through the bore is preferably from 5 to 80° C., more preferably from 10 to 70° C., most preferably from 30 to 60° C.

A carrier gas flows through the reaction zone. The carrier gas may be conducted through the reaction zone in cocurrent to the free-falling droplets of the monomer solution, i.e. from the top downward. After one pass, the gas is preferably recycled at least partly, preferably to an extent of at least 50%, more preferably to an extent of at least 75%, into the reaction zone as cycle gas. Typically, a portion of the carrier gas is discharged after each pass, preferably up to 10%, more preferably up to 3% and most preferably up to 1%.

The oxygen content of the carrier gas is preferably from 0.1 to 15% by volume, more preferably from 1 to 10% by volume, most preferably from 2 to 7% by weight. In the scope of the present invention it is also possible to use a carrier gas which is free of oxygen.

As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbon dioxide, argon, xenon, krypton, neon, helium, sulfurhexafluoride. Any mixture of carrier gases may be used. The carrier gas may also become loaded with water and/or acrylic acid vapors.

The gas velocity is preferably adjusted such that the flow in the reaction zone is directed, for example no convection currents opposed to the general flow direction are present, and is preferably from 0.1 to 2.5 m/s, more preferably from 0.3 to 1.5 m/s, even more preferably from 0.5 to 1.2 m/s, most preferably from 0.7 to 0.9 m/s.

The gas entrance temperature, i.e. the temperature with which the gas enters the reaction zone, is preferably from 160 to 200° C., more preferably from 165 to 195° C., even more preferably from 170 to 190° C., most preferably from 175 to 185° C.

The steam content of the gas that enters the reaction zone is preferably from 0.01 to 0.15 kg per kg dry gas, more from 0.02 to 0.12 kg per kg dry gas, most from 0.03 to 0.10 kg per kg dry gas.

The gas entrance temperature is controlled in such a way that the gas exit temperature, i.e. the temperature with which the gas leaves the reaction zone, is less than 150° C., preferably from 90 to 140° C., more preferably from 100 to 130° C., even more preferably from 105 to 125° C., most preferably from 110 to 120° C.

The steam content of the gas that leaves the reaction zone is preferably from 0.02 to 0.30 kg per kg dry gas, more from 0.04 to 0.28 kg per kg dry gas, most from 0.05 to 0.25 kg per kg dry gas.

The water-absorbent polymer particles can be divided into three categories: water-absorbent polymer particles of Type 1 are particles with one cavity, water-absorbent polymer particles of Type 2 are particles with more than one cavity, and water-absorbent polymer particles of Type 3 are solid particles with no visible cavity.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having more than one cavity (Type 2) show an improved mechanical stability.

The reaction can be carried out under elevated pressure or under reduced pressure, preferably from 1 to 100 mbar below ambient pressure, more preferably from 1.5 to 50 mbar below ambient pressure, most preferably from 2 to 10 mbar below ambient pressure.

The reaction off-gas, i.e. the gas leaving the reaction zone, may be cooled in a heat exchanger. This condenses water and unconverted monomer a). The reaction off-gas can then be reheated at least partly and recycled into the reaction zone as cycle gas. A portion of the reaction off-gas can be discharged and replaced by fresh gas, in which case water and unconverted monomers a) present in the reaction off-gas can be removed and recycled.

Particular preference is given to a thermally integrated system, i.e. a portion of the waste heat in the cooling of the off-gas is used to heat the cycle gas.

Deposits on the reactor walls can be removed by use of any available vibrating or knocking means.

The reactors can be trace-heated. In this case, the trace heating is adjusted such that the wall temperature is at least 5° C. above the internal surface temperature and condensation on the surfaces is reliably prevented.

Thermal Posttreatment

The formed water-absorbent polymer particles are thermal posttreated in a fluidized bed. In a preferred embodiment of the present invention an internal fluidized bed is used. An internal fluidized bed means that the product of the dropletization polymerization is accumulated in a fluidized bed below the reaction zone.

The residual monomers can be removed during the thermal posttreatment. What is important here is that the water-absorbent polymer particles are not too dry. In the case of excessively dry particles, the residual monomers decrease only insignificantly. Too high a water content increases the caking tendency of the water-absorbent polymer particles.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.3 to 2.5 m/s, more preferably from 0.4 to 2.0 m/s, most preferably from 0.5 to 1.5 m/s.

The pressure drop over the bottom of the internal fluidized bed is preferably from 1 to 100 mbar, more preferably from 3 to 50 mbar, most preferably from 5 to 25 mbar.

The moisture content of the water-absorbent polymer particles at the end of the thermal posttreatment is preferably from 1 to 20% by weight, more preferably from 2 to 15% by weight, even more preferably from 3 to 12% by weight, most preferably 5 to 8% by weight.

The temperature of the water-absorbent polymer particles during the thermal posttreatment is from 20 to 120° C., preferably from 40 to 100° C., more preferably from 50 to 95° C., even more preferably from 55 to 90° C., most preferably from 60 to 80° C.

The average residence time in the internal fluidized bed is from 10 to 300 minutes, preferably from 60 to 270 minutes, more preferably from 40 to 250 minutes, most preferably from 120 to 240 minutes.

The condition of the fluidized bed can be adjusted that the level of residual monomers of the water-absorbent polymers leaving the fluidized bed is preferably from 0.1 to 5% by weight, more preferably from 0.15 to 3% by weight, most preferably from 0.2 to 2% by weight.

The steam content of the gas is preferably from 0.005 to 0.25 kg per kg of dry gas, more preferably from 0.01 to 0.2 kg per kg of dry gas, most preferably from 0.02 to 0.15 kg per kg of dry gas.

By using additional steam the condition of the fluidized bed can be adjusted that the level of residual monomers of the water-absorbent polymers leaving the internal fluidized bed is preferably from 0.0001 to 1% by weight, more preferably from 0.0005 to 0.5% by weight, most preferably from 0.001 to 0.2% by weight.

In one preferred embodiment of the present invention the thermal posttreatment is completely or at least partially done in an external fluidized bed. The operating conditions of the external fluidized bed are within the scope for the internal fluidized bed as described above.

The level of residual monomers can be further reduced by an additional thermal posttreatment in a mixer with rotating mixing tools as described in WO 211/117215 A1.

The morphology of the water-absorbent polymer particles can also be controlled by the reaction conditions during thermal posttreatment. Water-absorbent polymer particles having a high amount of particles with one cavity (Type 1) can be prepared by using high product temperatures and short residence times. Water-absorbent polymer particles having a high amount of particles with more than one cavity (Type 2) can be prepared by using low product temperatures and long residence times.

The present invention is based upon the fact that the thermal posttreatment has a strong impact on the morphology of the formed water-absorbent polymer particles. Water-absorbent polymer particles having superior properties can be produced by adjusting the conditions of the thermal posttreatment.

Surface-Postcrosslinking

In the present invention the water-absorbent polymer particles may be surface-postcrosslinked for further improvement of the properties.

Surface-postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230. Also ethyleneoxide, aziridine, glycidol, oxetane and its derivatives may be used.

Polyvinylamine, polyamidoamines and polyvinylalcohole are examples of multifunctional polymeric surface-postcrosslinkers.

In addition, DE 40 20 780 C1 describes cyclic carbonates, DE 198 07 502 A1 describes 2-oxazolidone and its derivatives such as 2-hydroxyethyl-2-oxazolidone, DE 198 07 992 C1 describes bis- and poly-2-oxazolidinones, DE 198 54 573 A1 describes 2-oxotetrahydro-1,3-oxazine and its derivatives, DE 198 54 574 A1 describes N-acyl-2-oxazolidones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable surface-postcrosslinkers.

Particularly preferred postcrosslinkers are ethylene carbonate, glycerine carbonate, mixtures of propylene glycol, 1,3-propandiole, 1,4-butanediol, mixtures of 1,3-propandiole and 1,4-butanediole, ethylene glycol diglycidyl ether and reaction products of polyamides and epichlorohydrin.

Very particularly preferred postcrosslinkers are 2-hydroxyethyl-2-oxazolidone, 2-oxazolidone, ethylene carbonate and 1,3-propanediol.

In addition, it is also possible to use surface-postcrosslinkers which comprise additional polymerizable ethylenically unsaturated groups, as described in DE 37 13 601 A1.

The amount of postcrosslinker is preferably from 0.001 to 2% by weight, more preferably from 0.02 to 1% by weight, most preferably from 0.05 to 0.2% by weight, based in each case on the polymer.

The moisture content of the water-absorbent polymer particles prior to the thermal surface-postcrosslinking is preferably from 1 to 20% by weight, more preferably from 2 to 15% by weight, most preferably from 3 to 10% by weight.

The amount of alkylene carbonate is preferably from 0.1 to 10% by weight, more preferably from 0.5 to 7.5% by weight, most preferably from 1.0 to 5% by weight, based in each case on the polymer.

The content of residual monomers in the water-absorbent polymer particles prior to the coating with the alkylene carbonate is in the range from 0.1 to 10% by weight, preferably from 0.15 to 7.5% by weight, more preferably from 0.2 to 5% by weight, most preferably from 0.25 to 2.5% by weight.

In a preferred embodiment of the present invention, polyvalent cations are applied to the particle surface in addition to the surface-postcrosslinkers before, during or after the thermal surface-postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium, and mixtures thereof. Possible counterions are chloride, bromide, sulfate, hydrogensulfate, carbonate, hydrogencarbonate, nitrate, hydroxide, phosphate, hydrogenphosphate, dihydrogenphosphate and carboxylate, such as acetate, glycolate, tartrate, formiate, propionate, 3-hydroxypropionate, lactamide and lactate, and mixtures thereof. Aluminum sulfate, aluminum acetate, and aluminum lactate are preferred. Apart from metal salts, it is also possible to use polyamines and/or polymeric amines as polyvalent cations. A single metal salt can be used as well as any mixture of the metal salts and/or the polyamines above.

Preferred polyvalent cations and corresponding anions are disclosed in WO 2012/045705 A1 and are expressly incorporated herein by reference. Preferred polyvinylamines are disclosed in WO 2004/024816 A1 and are expressly incorporated herein by reference.

The amount of polyvalent cation used is, for example, from 0.001 to 1.5% by weight, preferably from 0.005 to 1% by weight, more preferably from 0.02 to 0.8% by weight, based in each case on the polymer.

The addition of the polyvalent metal cation can take place prior, after, or cocurrently with the surface-postcrosslinking. Depending on the formulation and operating conditions employed it is possible to obtain a homogeneous surface coating and distribution of the polyvalent cation or an inhomogenous typically spotty coating. Both types of coatings and any mixes between them are useful within the scope of the present invention.

The surface-postcrosslinking is typically performed in such a way that a solution of the surface-postcrosslinker is sprayed onto the hydrogel or the dry polymer particles. After the spraying, the polymer particles coated with the surface-postcrosslinker are dried thermally and cooled.

The spraying of a solution of the surface-postcrosslinker is preferably performed in mixers with moving mixing tools, such as screw mixers, disk mixers and paddle mixers. Suitable mixers are, for example, vertical Schugi Flexomix® mixers (Hosokawa Micron BV; Doetinchem; the Netherlands), Turbolizers® mixers (Hosokawa Micron BV; Doetinchem; the Netherlands), horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Ruberg continuous flow mixers and horizontal Pflugschar® plowshare mixers are preferred. The surface-postcrosslinker solution can also be sprayed into a fluidized bed.

The solution of the surface-postcrosslinker can also be sprayed on the water-absorbent polymer particles during the thermal posttreatment. In such case the surface-postcrosslinker can be added as one portion or in several portions along the axis of thermal posttreatment mixer. In one embodiment it is preferred to add the surface-postcrosslinker at the end of the thermal posttreatment step. As a particular advantage of adding the solution of the surface-postcrosslinker during the thermal posttreatment step it may be possible to eliminate or reduce the technical effort for a separate surface-postcrosslinker addition mixer.

The surface-postcrosslinkers are typically used as an aqueous solution. The addition of nonaqueous solvent can be used to adjust the penetration depth of the surface-postcrosslinker into the polymer particles.

The thermal surface-postcrosslinking is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Nara paddle driers and, in the case of low process temperatures (<160° C.) for example, when using polyfunctional epoxides, Holo-Flite® dryers are preferred. Moreover, it is also possible to use fluidized bed dryers. In the latter case the reaction times may be shorter compared to other embodiments.

When a horizontal dryer is used then it is often advantageous to set the dryer up with an inclined angle of a few degrees vs. the earth surface in order to impart proper product flow through the dryer. The angle can be fixed or may be adjustable and is typically between 0 to 10 degrees, preferably 1 to 6 degrees, most preferably 2 to 4 degrees.

In one embodiment of the present invention a contact dryer is used that has two different heating zones in one apparatus. For example Nara paddle driers are available with just one heated zone or alternatively with two heated zones. The advantage of using a two or more heated zone dryer is that different phases of the thermal post-treatment and/or of the post-surface-crosslinking can be combined.

In one preferred embodiment of the present invention a contact dryer with a hot first heating zone is used which is followed by a temperature holding zone in the same dryer. This set up allows a quick rise of the product temperature and evaporation of surplus liquid in the first heating zone, whereas the rest of the dryer is just holding the product temperature stable to complete the reaction.

In another preferred embodiment of the present invention a contact dryer with a warm first heating zone is used which is then followed by a hot heating zone. In the first warm zone the thermal post-treatment is affected or completed whereas the surface-postcrosslinking takes place in the subsequential hot zone.

In a typical embodiment a paddle heater with just one temperature zone is employed.

A person skilled in the art will depending on the desired finished product properties and the available base polymer qualities from the polymerization step choose any one of these set ups.

The thermal surface-postcrosslinking can be effected in the mixer itself, by heating the jacket, blowing in warm air or steam. Equally suitable is a downstream dryer, for example a shelf dryer, a rotary tube oven or a heatable screw. It is particularly advantageous to mix and dry in a fluidized bed dryer.

Preferred thermal surface-postcrosslinking temperatures are in the range from 100 to 180° C., preferably from 120 to 170° C., more preferably from 130 to 165° C., most preferably from 140 to 160° C. The preferred residence time at this temperature in the reaction mixer or dryer is preferably at least 5 minutes, more preferably at least 20 minutes, most preferably at least 40 minutes, and typically at most 120 minutes.

It is preferable to cool the polymer particles after thermal surface-postcrosslinking. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures in the range from 20 to 150° C., preferably from 40 to 120° C., more preferably from 60 to 100° C., most preferably from 70 to 90° C. Cooling using warm water is preferred, especially when contact coolers are used.

Coating

To improve the properties, the water-absorbent polymer particles can be coated and/or optionally moistened. The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the surface-postcrosslinked water-absorbent polymer particles. Suitable coatings for controlling the acquisition behavior and improving the permeability (SFC or GBP) are, for example, inorganic inert substances, such as water-insoluble metal salts, organic polymers, cationic polymers, anionic polymers and polyvalent metal cations. Suitable coatings for improving the color stability are, for example reducing agents, chelating agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20. Preferred coatings are aluminium dihydroxy monoacetate, aluminium sulfate, aluminium lactate, aluminium 3-hydroxypropionate, zirconium acetate, citric acid or its water soluble salts, di- and mono-phosphoric acid or their water soluble salts, Blancolen®, Brüggolite® FF7, Cublen® and Span® 20.

If salts of the above acids are used instead of the free acids then the preferred salts are alkalimetal, earth alkali metal, aluminum, zirconium, titanium, zinc and ammonium salts.

Under the trade name Cublen® (Zschimmer & Schwarz Mohsdorf GmbH & Co KG; Burgstädt; Germany) the following acids and/or their alkali metal salts (preferably Na and K-salts) are available and may be used within the scope of the present invention for example to impart colorstability to the finished product:

1-Hydroxyethane-1,1-diphosphonic acid, Amino-tris (methylene phosphonic acid), Ethylenediamine-tetra(methylene phosphonic acid), Diethylenetriamine-penta(methylene phosphonic acid), Hexamethylene diamine-tetra (methylenephosphonic acid), Hydroxyethyl-amino-di (methylene phosphonic acid), 2-Phosphonobutane-1,2,4-tricarboxylic acid, Bis(hexamethylenetriamine penta (methylene phosphonic acid)).

Most preferably 1-Hydroxyethane-1,1-diphosphonic acid or its salts with sodium, potassium, or ammonium are employed. Any mixture of the above Cublenes® can be used.

Alternatively, any of the chelating agents described before for use in the polymerization can be coated onto the finished product.

Suitable inorganic inert substances are silicates such as montmorillonite, kaolinite and talc, zeolites, activated carbons, polysilicic acids, magnesium carbonate, calcium carbonate, calcium phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the water-absorbent polymer particles are coated with inorganic inert substances, the amount of inorganic inert substances used, based on the water-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoro-ethylene. Other examples are styrene-isoprene-styrene block-copolymers or styrene-butadiene-styrene block-copolymers. Another example are silanole-group bearing polyvinylalcoholes available under the trade name Poval® R (Kuraray Europe GmbH; Frankfurt; Germany).

Suitable cationic polymers are polyalkylenepolyamines, cationic derivatives of polyacrylamides, polyethyleneimines and polyquaternary amines.

Polyquaternary amines are, for example, condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or polyfunctional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent, as dispersion in an aqueous or water-miscible dispersant or in substance.

When the water-absorbent polymer particles are coated with a cationic polymer, the use amount of cationic polymer based on the water-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable anionic polymers are polyacrylates (in acidic form or partially neutralized as salt), copolymers of acrylic acid and maleic acid available under the trade name Sokalan® (BASF SE; Ludwigshafen; Germany), and polyvinylalcohols with built in ionic charges available under the trade name Poval® K (Kuraray Europe GmbH; Frankfurt; Germany).

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, acetate, formiate, propionate, nitrate and sulfate. The metal salts are preferably used as a solution or as a stable aqueous colloidal dispersion. The solvents used for the metal salts may be water, alcohols, ethylene carbonate, propylene carbonate, dimethylformamide, dimethyl sulfoxide and mixtures thereof. Particular preference is given to water and water/alcohol mixtures, such as water/methanol, water/isopropanol, water/1,3-propanediole, water/1,2-propandiole/1,4-butanediole or water/propylene glycol.

When the water-absorbent polymer particles are coated with a polyvalent metal cation, the amount of polyvalent metal cation used, based on the water-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophosphite, salts of sulfinic acids, for example the disodium salt of 2-hydroxy-2-sulfinatoacetic acid, and addition products of aldehydes, for example the disodium salt of 2-hydroxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Bruggemann Chemicals; Heilbronn; Germany). Also useful is the purified 2-hydroxy-2-sulfonatoacetic acid and its sodium salts, available under the trade name Blancolen® from the same company.

The reducing agents are typically used in the form of a solution in a suitable solvent, preferably water. The reducing agent may be used as a pure substance or any mixture of the above reducing agents may be used.

When the water-absorbent polymer particles are coated with a reducing agent, the amount of reducing agent used, based on the water-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the water-absorbent polymer particles only insignificantly. The polyols are preferably used as a solution in aqueous or water-miscible solvents.

When the water-absorbent polymer particles are coated with a polyol, the use amount of polyol, based on the water-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Moreover, it is also possible to use a fluidized bed for mixing.

Agglomeration

The water-absorbent polymer particles can further selectivily be agglomerated. The agglomeration can take place after the polymerization, the thermal postreatment, the thermal surface-postcrosslinking or the coating.

Useful agglomeration assistants include water and water-miscible organic solvents, such as alcohols, tetrahydrofuran and acetone; water-soluble polymers can be used in addition.

For agglomeration a solution comprising the agglomeration assistant is sprayed onto the water-absorbing polymeric particles. The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

Combination of Thermal Posttreatment, Surface-Postcrosslinking and Optionally Coating In a preferred embodiment of the present invention the steps of thermal posttreatment and thermal surface-postcrosslinking are combined in one process step. Such combination allows the use of low cost equipment and moreover the process can be run at low temperatures, that is cost-efficient and avoids discoloration and loss of performance properties of the finished product by thermal degradation.

The mixer may be selected from any of the equipment options cited in the thermal posttreatment section. Ruberg continuous flow mixers, Becker shovel mixers and Pflugschar® plowshare mixers are preferred.

In this particular preferred embodiment the surface-postcrosslinking solution is sprayed onto the water-absorbent polymer particles under agitation.

Following the thermal posttreatment/surface-postcrosslinking the water-absorbent polymer particles are dried to the desired moisture level and for this step any dryer cited in the surface-postcrosslinking section may be selected. However, as only drying needs to be accomplished in this particular preferred embodiment it is possible to use simple and low cost heated contact dryers like a heated screw dryer, for example a Holo-Flite® dryer (Metso Minerals Industries Inc.; Danville; U.S.A.). Alternatively a fluidized bed may be used. In cases where the product needs to be dried with a predetermined and narrow residence time it is possible to use torus disc dryers or paddle dryers, for example a Nara paddle dryer (NARA Machinery Europe; Frechen; Germany).

In a preferred embodiment of the present invention, polyvalent cations cited in the surface-postcrosslinking section are applied to the particle surface before, during or after addition of the surface-postcrosslinker by using different addition points along the axis of a horizontal mixer.

In a very particular preferred embodiment of the present invention the steps of thermal posttreatment, surface-postcrosslinking, and coating are combined in one process step. Suitable coatings are cationic polymers, surfactants, and inorganic inert substances that are cited in the coating section. The coating agent can be applied to the particle surface before, during or after addition of the surface-postcrosslinker also by using different addition points along the axis of a horizontal mixer.

The polyvalent cations and/or the cationic polymers can act as additional scavengers for residual surface-postcrosslinkers. In a preferred embodiment of the present invention the surface-postcrosslinkers are added prior to the polyvalent cations and/or the cationic polymers to allow the surface-postcrosslinker to react first.

The surfactants and/or the inorganic inert substances can be used to avoid sticking or caking during this process step under humid atmospheric conditions. A preferred surfactant is Span® 20. Preferred inorganic inert substances are precipitated silicas and fumed silicas in form of powder or dispersion.

The amount of total liquid used for preparing the solutions/dispersions is typically from 0.01% to 25% by weight, preferably from 0.5% to 12% by weight, more preferably from 2% to 7% by weight, most preferably from 3% to 6% by weight, in respect to the weight amount of water-absorbent polymer particles to be processed.

Preferred embodiments are depicted in FIGS. 1 to 12.
FIG. 1: Process scheme (without external fluidized bed)
FIG. 2: Process scheme (with external fluidized bed)
FIG. 3: Arrangement of the T_outlet measurement
FIG. 4: Arrangement of the dropletizer units
FIG. 5: Dropletizer unit (longitudinal cut)
FIG. 6: Dropletizer unit (cross sectional view)
FIG. 7: Bottom of the internal fluidized bed (top view)
FIG. 8: openings in the bottom of the internal fluidized bed
FIG. 9: Rake stirrer for the intern fluidized bed (top view)
FIG. 10: Rake stirrer for the intern fluidized bed (cross sectional view)
FIG. 11: Process scheme (surface-postcrosslinking)
FIG. 12: Process scheme (surface-postcrosslinking and coating)

The reference numerals have the following meanings:
1 Drying gas inlet pipe
2 Drying gas amount measurement
3 Gas distributor
4 Dropletizer units
5 Cocurrent spray dryer, cylindrical part
6 Cone
7 T_outlet measurement
8 Tower offgas pipe
9 Baghouse filter
10 Ventilator
11 Quench nozzles
12 Condenser column, counter current cooling
13 Heat exchanger
14 Pump
15 Pump
16 Water outlet
17 Ventilator
18 Offgas outlet
19 Nitrogen inlet
20 Heat exchanger
21 Ventilator
22 Heat exchanger
23 Steam injection via nozzles
24 Water loading measurement
25 Conditioned internal fluidized bed gas
26 Internal fluidized bed product temperature measurement
27 Internal fluidized bed
28 Rotary valve
29 Sieve
30 End product
31 Static mixer
32 Static mixer
33 Initiator feed
34 Initiator feed
35 Monomer feed
36 Fine particle fraction outlet to rework
37 External fluidized bed
38 Ventilator
39 External fluidized bed offgas outlet to baghouse filter
40 Rotary valve
41 Filtered air inlet
42 Ventilator
43 Heat exchanger
44 Steam injection via nozzle
45 Water loading measurement
46 Conditioned external fluidized bed gas
47 T_outlet measurement (average temperature out of 3 measurements around tower circumference)
48 Dropletizer unit
49 Monomer premixed with initiator feed
50 Spray dryer tower wall
51 Dropletizer unit outer pipe
52 Dropletizer unit inner pipe
53 Dropletizer cassette
54 Teflon block
55 Valve
56 Monomer premixed with initiator feed inlet pipe connector
57 Droplet plate
58 Counter plate
59 Flow channels for temperature control water
60 Dead volume free flow channel for monomer solution
61 Dropletizer cassette stainless steel block
62 Bottom of the internal fluidized bed with four segments
63 Split openings of the segments
64 Rake stirrer
65 Prongs of the rake stirrer
66 Mixer
67 Optional coating feed 68 Postcrosslinker feed
69 Thermal dryer (surface-postcrosslinking)
70 Cooler
71 Optional coating/water feed
72 Coater
73 Coating/water feed The drying gas is fed via a gas distributor (3) at the top of the spray dryer as shown in FIG. 1. The drying gas is partly recycled (drying gas loop) via a baghouse filter (9) and a condenser column (12). The pressure inside the spray dryer is below ambient pressure.

Figure 3:
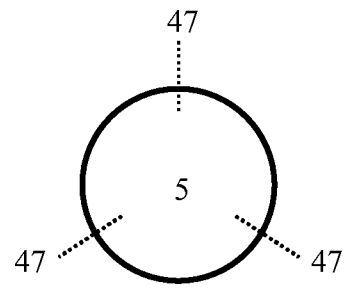

The spray dryer outlet temperature is preferably measured at three points around the circumference at the end of the cylindrical part as shown in FIG. 3. The single measurements (47) are used to calculate the average cylindrical spray dryer outlet temperature.

The product accumulated in the internal fluidized bed (27). Conditioned internal fluidized bed gas is fed to the internal fluidized bed (27) via line (25). The relative humidity of the internal fluidized bed gas is preferably controlled by adding steam via line (23).

The spray dryer offgas is filtered in baghouse filter (9) and sent to a condenser column (12) for quenching/cooling. After the baghouse filter (9) a recuperation heat exchanger system for preheating the gas after the condenser column (12) can be used. The baghouse filter (9) may be trace-heated on a temperature of preferably from 80 to 180° C., more preferably from 90 to 150° C., most preferably from 100 to 140° C. Excess water is pumped out of the condenser column (12) by controlling the (constant) filling level inside the condenser column (12). The water inside the condenser column (12) is cooled by a heat exchanger (13) and pumped counter-current to the gas via quench nozzles (11) so that the temperature inside the condenser column (12) is preferably from 20 to 100° C., more preferably from 25 to 80° C., most preferably from 30 to 60° C. The water inside the condenser column (12) is set to an alkaline pH by dosing a neutralizing agent to wash out vapors of monomer a). Aqueous solution from the condenser column (12) can be sent back for preparation of the monomer solution.

The condenser column offgas is split to the drying gas inlet pipe (1) and the conditioned internal fluidized bed gas (25). The gas temperatures are controlled via heat exchangers (20) and (22). The hot drying gas is fed to the cocurrent spray dryer via gas distributor (3). The gas distributor (3) consists preferably of a set of plates providing a pressure drop of preferably 1 to 100 mbar, more preferably 2 to 30 mbar, most preferably 4 to 20 mbar, depending on the drying gas amount. Turbulences and/or a centrifugal velocity can also be introduced into the drying gas if desired by using gas nozzles or baffle plates.

Conditioned internal fluidized bed gas is fed to the internal fluidized bed (27) via line (25). The relative humidity of the external fluidized bed gas is preferably controlled by adding steam via line (23). To prevent any condensation the steam is added together with the internal fluidized bed into the heat exchanger (22). The product holdup in the internal fluidized bed (27) can be controlled via rotational speed of the rotary valve (28).

The product is discharged from the internal fluidized bed (27) via rotary valve (28). The product holdup in the internal fluidized bed (27) can be controlled via rotational speed of the rotary valve (28). The sieve (29) is used for sieving off overs/lumps.

The monomer solution is preferably prepared by mixing first monomer a) with a neutralization agent and secondly with crosslinker b). The temperature during neutralization is controlled to preferably from 5 to 60° C., more preferably from 8 to 40° C., most preferably from 10 to 30° C., by using a heat exchanger and pumping in a loop. A filter unit is preferably used in the loop after the pump. The initiators are metered into the monomer solution upstream of the dropletizer by means of static mixers (31) and (32) via lines (33) and (34) as shown in FIG. 1. Preferably a peroxide solution having a temperature of preferably from 5 to 60° C., more preferably from 10 to 50° C., most preferably from 15 to 40° C., is added via line (33) and preferably an azo initiator solution having a temperature of preferably from 2 to 30° C., more preferably from 3 to 15° C., most preferably from 4 to 8° C., is added via line (34). Each initiator is preferably pumped in a loop and dosed via control valves to each dropletizer unit. A second filter unit is preferably used after the static mixer (32). The mean residence time of the monomer solution admixed with the full initiator package in the piping before the droplet plates (57) is preferably less than 60 s, more preferably less than 30 s, most preferably less than 10 s.

Figure 4:
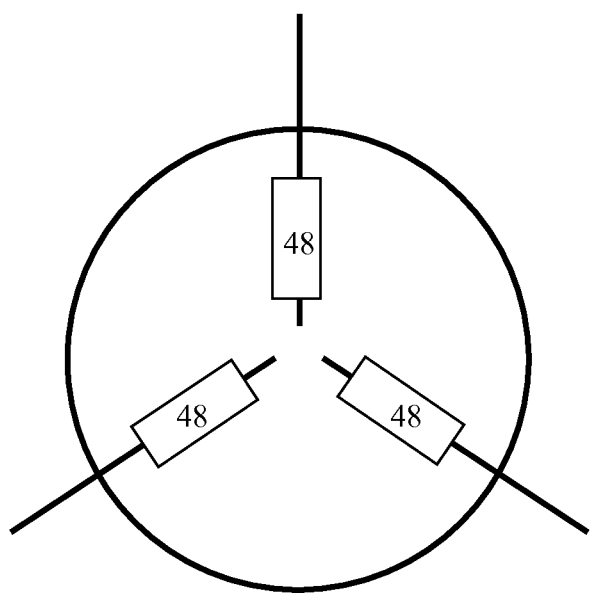

For dosing the monomer solution into the top of the spray dryer preferably three dropletizer units are used as shown in FIG. 4. However, any number of dropletizers can be used that is required to optimize the throughput of the process and the quality of the product. Hence, in the present invention at least one dropletizer is employed, and as many dropletizers as geometrically allowed may be used.

Figure 5:
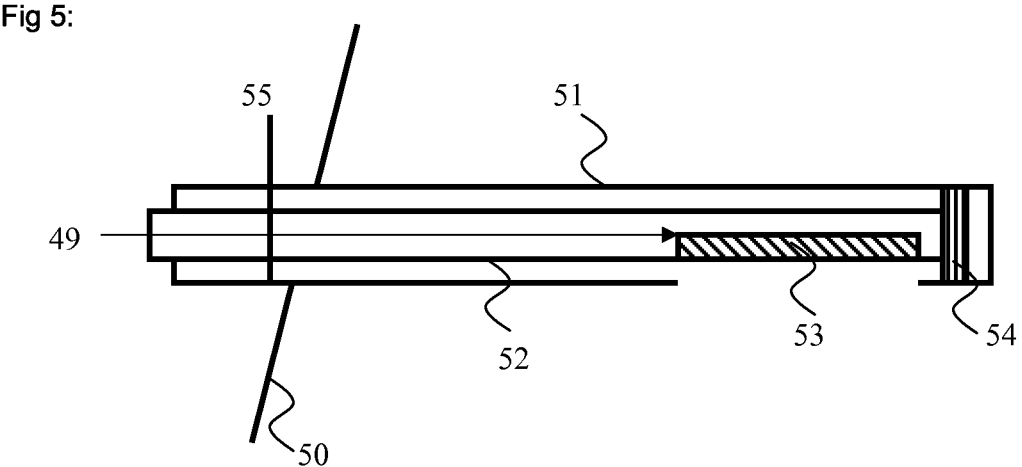

A dropletizer unit consists of an outer pipe (51) having an opening for the dropletizer cassette (53) as shown in FIG. 5. The dropletizer cassette (53) is connected with an inner pipe (52). The inner pipe (53) having a PTFE block (54) at the end as sealing can be pushed in and out of the outer pipe (51) during operation of the process for maintenance purposes.

Figure 6:
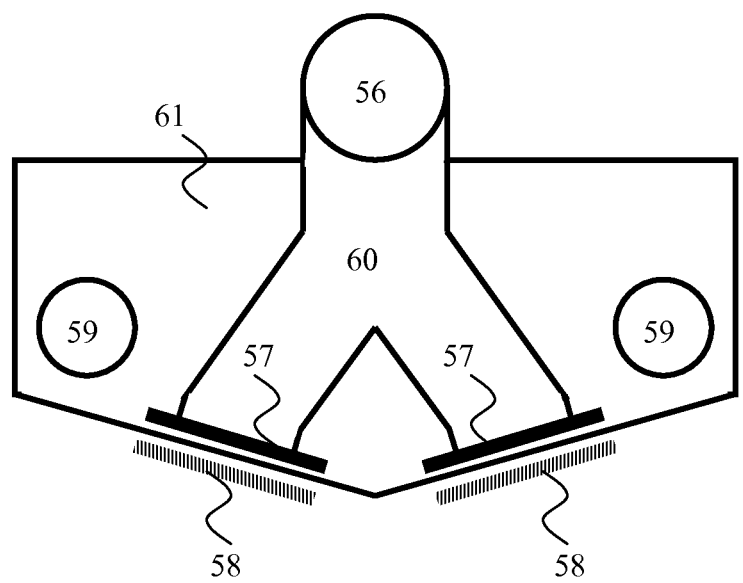

The temperature of the dropletizer cassette (61) is controlled to preferably 5 to 80° C., more preferably 10 to 70° C., most preferably 30 to 60° C., by water in flow channels (59) as shown in FIG. 6.

The dropletizer cassette has preferably from 10 to 1500, more preferably from 50 to 1000, most preferably from 100 to 500, bores having a diameter of preferably from 50 to 500 µm, more preferably from 100 to 300 µm, most preferably from 150 to 250 µm. The bores can be of circular, rectangular, triangular or any other shape. Circular bores are preferred. The ratio of bore length to bore diameter is preferably from 0.5 to 10, more preferably from 0.8 to 5, most preferably from 1 to 3. The droplet plate (57) can have a greater thickness than the bore length when using an inlet bore channel. The droplet plate (57) is preferably long and narrow as disclosed in WO 2008/086976 A1. Multiple rows of bores per droplet plate can be used, preferably from 1 to 20 rows, more preferably from 2 to 5 rows.

The dropletizer cassette (61) consists of a flow channel (60) having essential no stagnant volume for homogeneous distribution of the premixed monomer and initiator solutions and two droplet plates (57). The droplet plates (57) have an angled configuration with an angle of preferably from 1 to 90°, more preferably from 3 to 45°, most preferably from 5 to 20°. Each droplet plate (57) is preferably made of a heat and/or chemically resistant material, such as stainless steel, polyether ether ketone, polycarbonate, polyarylsulfone, such as polysulfone, or polyphenylsulfone, or fluorous polymers, such as perfluoroalkoxyethylene, polytetrafluoroethylene, polyvinylidenfluorid, ethylene-chlorotrifluoroethylene copolymers, ethylene-tetrafluoroethylene copolymers and fluorinated polyethylene. Coated droplet plates as disclosed in WO 2007/031441 A1 can also be used. The choice of material for the droplet plate is not limited except that droplet formation must work and it is preferable to use materials which do not catalyze the start of polymerization on its surface.

The throughput of monomer including initiator solutions per dropletizer unit is preferably from 150 to 2500 kg/h, more preferably from 200 to 1000 kg/h, most preferably from 300 to 600 kg/h. The throughput per bore is preferably from 0.1 to 10 kg/h, more preferably from 0.5 to 5 kg/h, most preferably from 0.7 to 2 kg/h.

The start-up of the cocurrent spray dryer (5) can be done in the following sequence:
  starting the condenser column (12),
  starting the ventilators (10) and (17),
  starting the heat exchanger (20),
  heating up the drying gas loop up to 95° C.,
  starting the nitrogen feed via the nitrogen inlet (19),
  waiting until the residual oxygen is below 4% by weight,
  heating up the drying gas loop,
  at a temperature of 105° C. starting the water feed (not shown) and
  at target temperature stopping the water feed and starting the monomer feed via dropletizer unit (4)

The shut-down of the cocurrent spray dryer (5) can be done in the following sequence:
  stopping the monomer feed and starting the water feed (not shown),
  shut-down of the heat exchanger (20),
  cooling the drying gas loop via heat exchanger (13),
  at a temperature of 105° C. stopping the water feed,
  at a temperature of 60° C. stopping the nitrogen feed via the nitrogen inlet (19) and
  feeding air into the drying gas loop (not shown)

To prevent damages the cocurrent spray dryer (5) must be heated up and cooled down very carefully. Any quick temperature change must be avoided.

Figure 7:
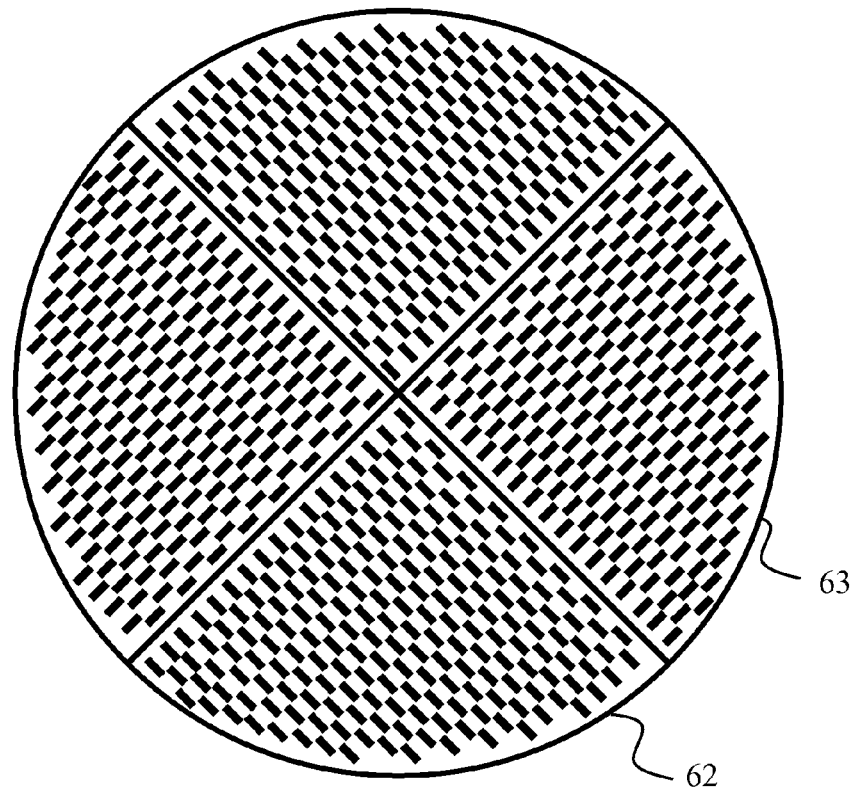
Figure 8:
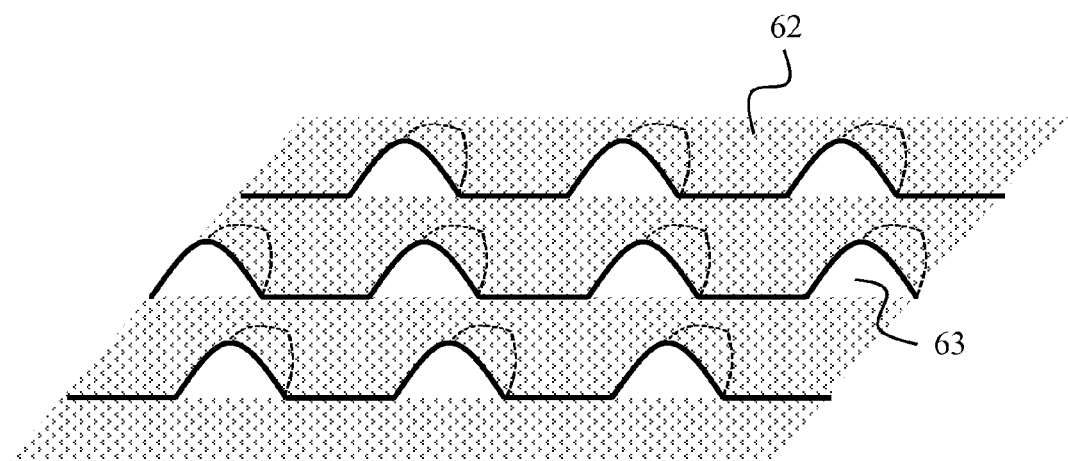

The openings in the bottom of the internal fluidized bed may be arranged in a way that the water-absorbent polymer particles flow in a cycle as shown in FIG. 7. The bottom shown in FIG. 7 comprises of four segments (62). The openings (63) in the segments (62) are in the shape of slits that guides the passing gas stream into the direction of the next segment (62). FIG. 8 shows an enlarged view of the openings (63).

The opening may have the shape of holes or slits. The diameter of the holes is preferred from 0.1 to 10 mm, more preferred from 0.2 to 5 mm, most preferred from 0.5 to 2 mm. The slits have a length of preferred from 1 to 100 mm, more preferred from 2 to 20 mm, most preferred from 5 to 10 mm, and a width of preferred from 0.5 to 20 mm, more preferred from 1 to 10 mm, most preferred from 2 to 5 mm.

Figure 9:
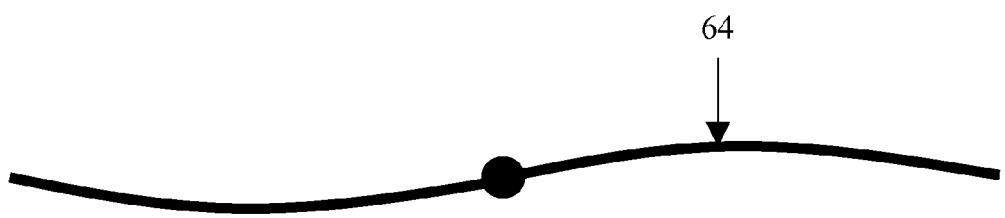
Figure 10:
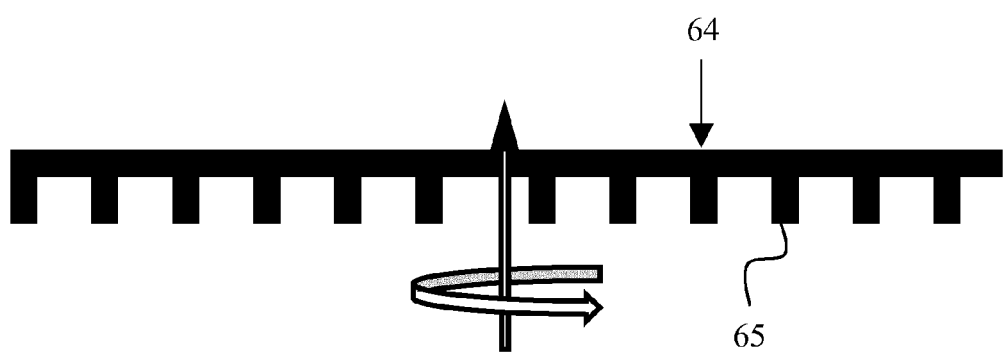
Figure 11:
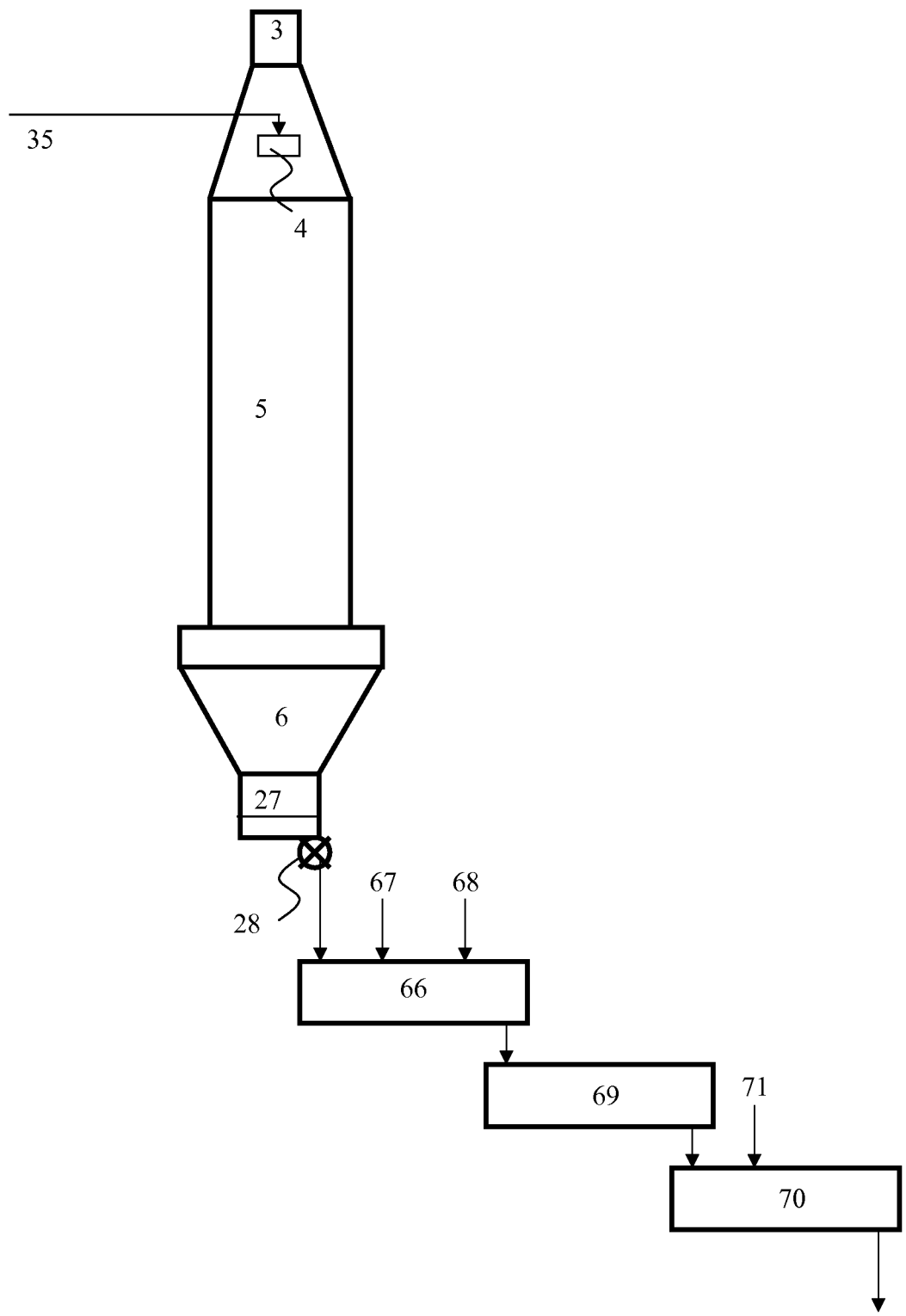
Figure 12:
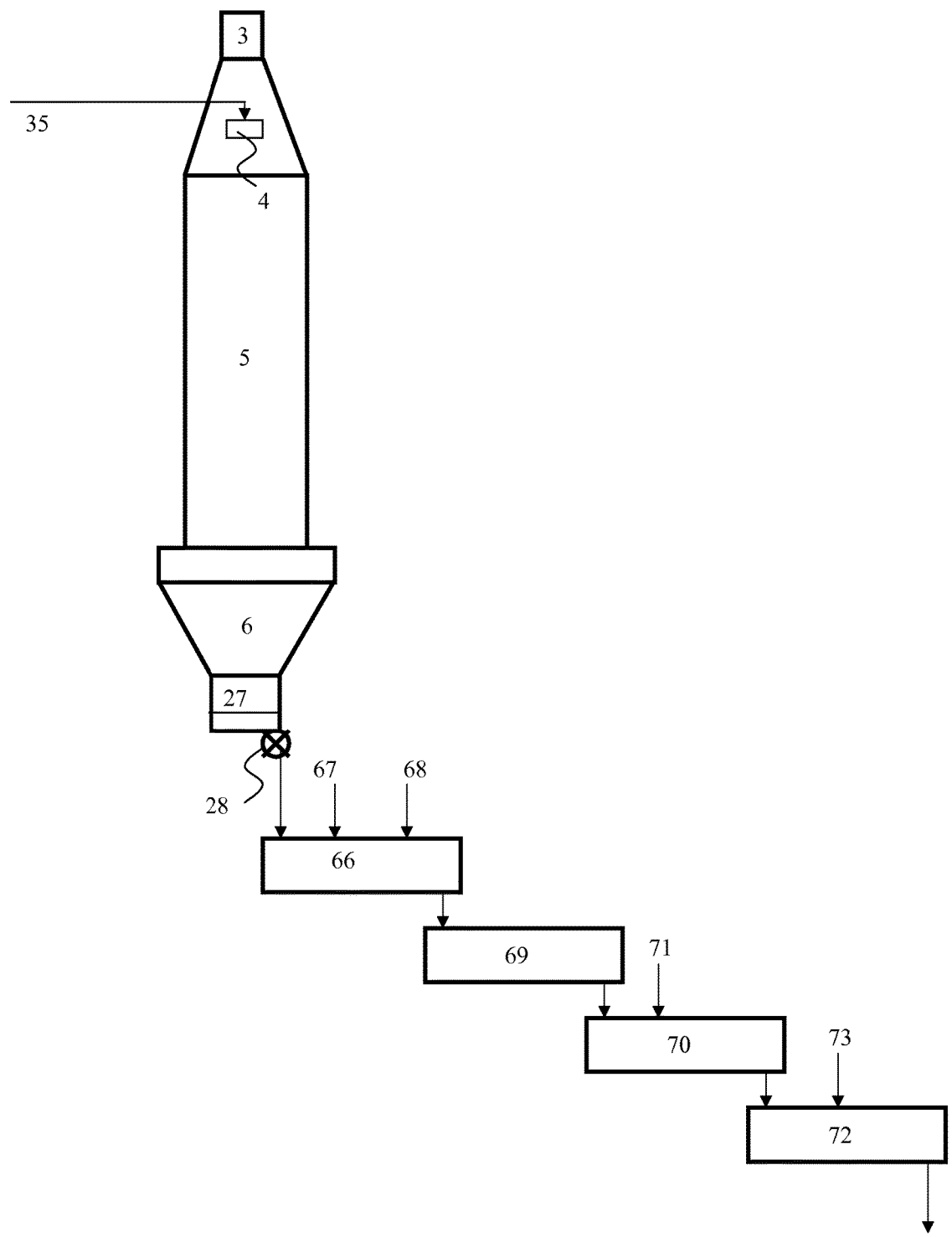

FIG. 9 and FIG. 10 show a rake stirrer (64) that may be used in the internal fluidized bed. The prongs (65) of the rake have a staggered arrangement. The speed of rake stirrer is preferably from 0.5 to 20 rpm, more preferably from 1 to 10 rpm most preferably from 2 to 5 rpm.

For start-up the internal fluidized bed may be filled with a layer of water-absorbent polymer particles, preferably 5 to 50 cm, more preferably from 10 to 40 cm, most preferably from 15 to 30 cm.

Water-absorbent Polymer Particles

The present invention further provides water-absorbent polymer particles obtainable by the process according to the invention.

The inventive water-absorbent polymer particles have a mean sphericity from preferably from 0.80 to 0.95, more preferably from 0.82 to 0.93, even more preferably from 0.84 to 0.91, most preferably from 0.85 to 0.90. The sphericity (SPHT) is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technology GmbH; Haan; Germany):

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. To record the particles, the so-called CCD-zoom camera (CAM-Z) is used. To control the metering channel, a surface coverage fraction in the detection window of the camera (transmission) of 0.5% is predefined.

Water-absorbent polymer particles with relatively low sphericity are obtained by reverse suspension polymerization when the polymer beads are agglomerated during or after the polymerization.

The water-absorbent polymer particles prepared by customary solution polymerization (gel polymerization) are ground and classified after drying to obtain irregular polymer particles. The mean sphericity of these polymer particles is between approx. 0.72 and approx. 0.78.

The inventive water-absorbent polymer particles have a content of hydrophobic solvent of preferably less than 0.005% by weight, more preferably less than 0.002% by weight and most preferably less than 0.001% by weight. The content of hydrophobic solvent can be determined by gas chromatography, for example by means of the headspace technique. A hydrophobic solvent within the scope of the present invention is either immiscible in water or only sparingly miscible. Typical examples of hydrophobic solvents are pentane, hexane, cyclohexane, toluene.

Water-absorbent polymer particles which have been obtained by reverse suspension polymerization still comprise typically approx. 0.01% by weight of the hydrophobic solvent used as the reaction medium.

The inventive water-absorbent polymer have a dispersant content of preferably less than 0.5% by weight, more preferably less than 0.1% by weight and most preferably less than 0.05% by weight.

Water-absorbent polymer particles which have been obtained by reverse suspension polymerization still comprise typically at least 1% by weight of the dispersant, i.e. ethylcellulose, used to stabilize the suspension.

The inventive water-absorbent polymer particles have a bulk density preferably from 0.6 to 1 g/cm$^3$, more preferably from 0.65 to 0.9 g/cm$^3$, most preferably from 0.68 to 0.8 g/cm$^3$.

The average particle diameter (APD) of the inventive water-absorbent polymer particles is preferably from 200 to 550 µm, more preferably from 250 to 500 µm, most preferably from 350 to 450 µm.

The particle diameter distribution (PDD) of the inventive water-absorbent polymer particles is preferably less than 0.7, more preferably less than 0.65, more preferably less than 0.6.

The inventive water-absorbent polymer particles have a centrifuge retention capacity (CRC) of preferably from 35 to 100 g/g, more preferably from 40 to 80 g/g, most preferably from 45 to 60 g/g.

The inventive water-absorbent polymer particles have a HC 60 value of preferably at least 80, more preferably of at least 85, most preferably of at least 90.

The inventive water-absorbent polymer particles have an absorbency under a load of 21.0 g/cm$^2$ (AUL) of preferably from 15 to 60 g/g, more preferably from 20 to 50 g/g, most preferably from 25 to 40 g/g.

The level of extractable constituents of the inventive water-absorbent polymer particles is preferably from 0.1 to 30% by weight, more preferably from 0.5 to 25% by weight, most preferably from 1 to 20% by weight.

The inventive water-absorbent polymer particles can be mixed with other water-absorbent polymer particles prepared by other processes, i.e. solution polymerization.

Fluid-absorbent Articles

The present invention further provides fluid-absorbent articles. The fluid-absorbent articles comprise of
(A) an upper liquid-pervious layer
(B) a lower liquid-impervious layer
(C) a fluid-absorbent core between (A) and (B) comprising
  from 5 to 90% by weight fibrous material and from 10 to 95% by weight water-absorbent polymer particles of the present invention;
  preferably from 20 to 80% by weight fibrous material and from 20 to 80% by weight water-absorbent polymer particles of the present invention;
  more preferably from 30 to 75% by weight fibrous material and from 25 to 70% by weight water-absorbent polymer particles of the present invention;
  most preferably from 40 to 70% by weight fibrous material and from 30 to 60% by weight water-absorbent polymer particles of the present invention;
(D) an optional acquisition-distribution layer between (A) and (C), comprising
  from 80 to 100% by weight fibrous material and from 0 to 20% by weight water-absorbent polymer particles of the present invention;
  preferably from 85 to 99.9% by weight fibrous material and from 0.01 to 15% by weight water-absorbent polymer particles of the present invention;
  more preferably from 90 to 99.5% by weight fibrous material and from 0.5 to 10% by weight water-absorbent polymer particles of the present invention;
  most preferably from 95 to 99% by weight fibrous material and from 1 to 5% by weight water-absorbent polymer particles of the present invention;
(E) an optional tissue layer disposed immediately above and/or below (C); and
(F) other optional components.

Fluid-absorbent articles are understood to mean, for example, incontinence pads and incontinence briefs for adults or diapers for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapor breathability, dryness, wearing comfort and protection on the one side, and concerning liquid retention, rewet and prevention of wet through on the other side. The specific combination of these layers provides a fluid-absorbent article delivering both high protection levels as well as high comfort to the consumer.

The products as obtained by the present invention are also very suitable to be incorporated into low-fluff, low-fiber, fluff-less, or fiber-less hygiene article designs. Such designs and methods to make them are for example described in the following publications and literature cited therein and are expressly incorporated into the present invention: WO 2010/133529 A2, WO 2011/084981 A1, US 2011/0162989, US 2011/0270204, WO 2010/082373 A1, WO 2010/143635 A1, U.S. Pat. No. 6,972,011, WO 2012/048879 A1, WO 2012/052173 A1 and WO 2012/052172 A1.

The present invention further provides fluid-absorbent articles, comprising water-absorbent polymer particles of the present invention and less than 15% by weight fibrous material and/or adhesives in the absorbent core.

The water-absorbent polymer particles and the fluid-absorbent articles are tested by means of the test methods described below.

Methods:

The measurements should, unless stated otherwise, be carried out at an ambient temperature of 23±2° C. and a relative atmospheric humidity of 50±10%. The water-absorbent polymers are mixed thoroughly before the measurement.

Free Swell Rate (FSR)

1.00 g (=W1) of the dry water-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR\ [g/gs] = W2/(W1 \times t)$$

When the moisture content of the hydrogel-forming polymer is more than 3% by weight, however, the weight W1 must be corrected for this moisture content.

Vortex 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of water-absorbent polymer particles are added to the beaker as quickly as possible, starting a stop watch as addition begins. The stopwatch is stopped when the surface of the mixture becomes "still" that means the surface has no turbulence, and while the mixture may still turn, the entire surface of particles turns as a unit. The displayed time of the stopwatch is recorded as Vortex time.

Residual Monomers

The level of residual monomers in the water-absorbent polymer particles is determined by the EDANA recommended test method No. WSP 410.2-05 "Residual Monomers".

Particle Size Distribution

The particle size distribution of the water-absorbent polymer particles is determined with the Camziser® image analysis system (Retsch Technology GmbH; Haan; Germany).

For determination of the average particle diameter and the particle diameter distribution the proportions of the particle fractions by volume are plotted in cumulated form and the average particle diameter is determined graphically.

The average particle diameter (APD) here is the value of the mesh size which gives rise to a cumulative 50% by weight.

The particle diameter distribution (PDD) is calculated as follows:

$$PDD = \frac{x_2 - x_1}{APD},$$

wherein $x_1$ is the value of the mesh size which gives rise to a cumulative 90% by weight and $x_2$ is the value of the mesh size which gives rise to a cumulative 10% by weight.

Mean Sphericity

The mean sphericity is determined with the Camziser® image analysis system (Retsch Technology GmbH; Haan; Germany) using the particle diameter fraction from 100 to 1,000 μm.

Moisture Content

The moisture content of the water-absorbent polymer particles is determined by the EDANA recommended test method No. WSP 430.2-05 "Moisture Content".

Centrifuge Retention Capacity (CRC)

The centrifuge retention capacity of the water-absorbent polymer particles is determined by the EDANA recommended test method No. WSP 441.2-05 "Centrifuge Retention Capacity", wherein for higher values of the centrifuge retention capacity larger tea bags have to be used.

Absorbency Under No Load (AUNL)

The absorbency under no load of the water-absorbent polymer particles is determined analogously to the EDANA recommended test method No. WSP 442.2-05 "Absorption Under Pressure", except using a weight of 0.0 g/cm² instead of a weight of 21.0 g/cm².

Absorbency Under Load (AUL)

The absorbency under load of the water-absorbent polymer particles is determined by the EDANA recommended test method No. WSP 442.2-05 "Absorption Under Pressure".

Absorbency Under High Load (AUHL)

The absorbency under high load of the water-absorbent polymer particles is determined analogously to the EDANA recommended test method No. WSP 442.2-05 "Absorption Under Pressure", except using a weight of 49.2 g/cm² instead of a weight of 21.0 g/cm².

Bulk Density

The bulk density of the water-absorbent polymer particles is determined by the EDANA recommended test method No. WSP 460.2-05 "Density".

Extractables

The level of extractable constituents in the water-absorbent polymer particles is determined by the EDANA recommended test method No. WSP 470.2-05 "Extractables".

Color Value (CIE Color Numbers [L, a, b])

Measurement of the color value is done by means of a colorimeter model "LabScan XE S/N LX17309" (HunterLab; Reston; U.S.A.) according to the CIELAB procedure (Hunterlab, Volume 8, 1996, Issue 7, pages 1 to 4). Colors are described by the coordinates L, a, and b of a three-dimensional system. L characterizes the brightness, whereby L=0 is black and L=100 is white. The values for a and b describe the position of the color on the color axis red/green resp. yellow/blue, whereby positive a values stand for red colors, negative a values for green colors, positive b values for yellow colors, and negative b values for blue colors. The HC60 value is calculated according to the formula HC60=L−3b.

The measurement of the color value is in agreement with the tristimulus method according to DIN 5033-6.

The EDANA test methods are obtainable, for example, from the EDANA, Avenue Eugène Plasky 157, B-1030 Brussels, Belgium.

EXAMPLES

Preparation of the Base Polymer

Example 1

The process was performed in a concurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a baghouse filter (9) and a condenser column (12). Instead of the baghouse filter (9) any other filter and/or cyclone can be used. The drying gas was nitrogen that comprises from 1% to 4% by volume of residual oxygen: Before start of polymerization the drying gas loop was filled with nitrogen until the residual oxygen was below 4% by volume. The gas velocity of the drying gas in the cylindrical part of the spray dryer (5) was 0.79 m/s. The pressure inside the spray dryer was 4 mbar below ambient pressure.

The spray dryer outlet temperature was measured at three points around the circumference at the end of the cyclindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 118° C. by adjusting the gas inlet temperature via the heat exchanger (20). The gas inlet temperature was 168° C. and the steam content of the drying gas was 0.058 kg steam per kg dry gas.

The product accumulated in the internal fluidized bed (27) until the weir height was reached. Conditioned internal fluidized bed gas having a temperature of 120° C. and a steam content of 0.058 kg steam per kg dry gas was fed to the internal fluidized bed (27) via line (25). The gas velocity of the internal fluidized bed gas in the internal fluidized bed (27) was 0.65 m/s. The residence time of the product was 150 min. The temperature of the water-absorbent polymer particles in the internal fluidized bed was 80° C.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 45° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and [2,2'-azobis[2-(2-imidazolin-2-yl)propane]dihydrochloride solution together with Bruggolite FF7 having a temperature of 5° C. was added via line (44). Each initiator was pumped in a loop and dosed via control valves to each dropletizer unit. A second filter unit having a mesh size of 140 μm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 8° C. by water in flow channels (59) as shown in FIG. 6. The dropletizer cassette (61) had 256 bores having a diameter of 170 μm and a bore separation of 15 mm. The dropletizer cassette (61) consisted of a flow channel (60) having essential no stagnant volume for homogeneous distribution of the premixed monomer and initiator solutions and one droplet plate (57). The droplet plate (57) had an angled configuration with an angle of 3°. The droplet plate (57) was made of stainless steel and had a length of 630 mm, a width of 128 mm and a thickness of 1 mm.

The feed to the spray dryer consisted of 12.45% by weight of acrylic acid, 33.40% by weight of sodium acrylate, 0.022% by weight of 3-tuply ethoxylated glycerol triacrylate, 0.036 to 0.072% by weight of [2,2'-azobis[2-(2-imidazolin-2-yl)propane]dihydrochlorid, 0.0029% by weight of Bruggolite FF7, 0.054% by weight of sodiumperoxodisulfate and water. The degree of neutralization was 71%. The feed per bore was 1.6 kg/h.

The resulting water-absorbent polymer particles were analyzed. The results are summarized in Table 1.

TABLE 1

Effect of the azo initiator

| Example | Azo initiator | Bulk Density [g/cm³] | CRC [g/g] | AUNL [g/g] | AUL [g/g] | Residual Monomers [ppm] | Extractables [wt. %] | Moisture [wt. %] | FSR [g/gs] | L | a | b | HC 60 |
|---|---|---|---|---|---|---|---|---|---|---|---|---|---|
| 1a | 0.08*) | 0.74 | 32.6 | 37.5 | 24.2 | 15100 | 4.0 | 6.1 | 0.28 | 95.0 | 2.2 | 1.3 | 91.1 |
| 1b | 0.12*) | 0.73 | 36.6 | 44.8 | 24.8 | 13600 | 4.2 | 5.6 | 0.22 | 95.2 | 1.5 | 0.9 | 92.5 |
| 1c | 0.16*) | 0.76 | 47.0 | 55.1 | 25.1 | 11700 | 3.8 | 6.3 | 0.14 | 96.1 | 1.7 | 1.2 | 92.5 |

*)% by weight based on monomer a)

Example 2

The process was performed in a concurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 3 m and a weir height of 0.25 m.

The drying gas was feed via a gas distributor (3) at the top of the spray dryer. The drying gas was partly recycled (drying gas loop) via a baghouse filter (9) and a condenser column (12). Instead of the baghouse filter (9) any other filter and/or cyclone can be used. The drying gas was nitrogen that comprises from 1% to 4% by volume of residual oxygen: Before start of polymerization the drying gas loop was filled with nitrogen until the residual oxygen was below 4% by volume. The gas velocity of the drying gas in the cylindrical part of the spray dryer (5) was 0.62 m/s. The pressure inside the spray dryer was 4 mbar below ambient pressure.

The spray dryer outlet temperature was measured at three points around the circumference at the end of the cyclindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 116° C. by adjusting the gas inlet temperature via the heat exchanger (20). The gas inlet temperature was 167° C. and the steam content of the drying gas was 0.058 kg steam per kg dry gas.

The product accumulated in the internal fluidized bed (27) until the weir height was reached. Conditioned internal fluidized bed gas having a temperature of 123° C. and a steam content of 0.058 kg steam per kg dry gas was fed to the internal fluidized bed (27) via line (25). The gas velocity of the internal fluidized bed gas in the internal fluidized bed (27) was 0.65 m/s. The residence time of the product was 240 min. The temperature of the water-absorbent polymer particles in the internal fluidized bed was 84° C.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 45° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and [2,2'-azobis[2-(2-imidazolin-2-yl)propane]dihydrochloride solution together with Bruggolite FF7 having a temperature of 5° C. was added via line (44). Each initiator was pumped in a loop and dosed via control valves to each dropletizer unit. A second filter unit having a mesh size of 140 μm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 8° C. by water in flow channels (59) as shown in FIG. 6. The dropletizer cassette (61) had 256 bores having a diameter of 170 μm and a bore separation of 15 mm. The dropletizer cassette (61) consisted of a flow channel (60) having essential no stagnant volume for homogeneous distribution of the premixed monomer and initiator solutions and one droplet plate (57). The droplet plate (57) had an angled configuration with an angle of 3°. The droplet plate (57) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.018% by weight of 3-tuply ethoxylated glycerol triacrylate, 0.025% by weight of [2,2'-azobis[2-(2-imidazolin-2-yl)propane]dihydrochloride, 0.0036% by weight of Bruggolite FF7, 0.054 to 0.270% by weight of sodiumperoxodisulfate and water. The degree of neutralization was 71%. The feed per bore was 1.6 kg/h.

The resulting water-absorbent polymer particles were analyzed. The results are summarized in Table 2.

TABLE 2

Effect of the persulfate

| Example | Persulfate | Bulk Density [g/cm$^3$] | CRC [g/g] | AUNL [g/g] | AUL [g/g] | Residual Monomers [ppm] | Extractables [wt. %] | Moisture [wt. %] | FSR [g/gs] | L | a | b | HC 60 |
|---|---|---|---|---|---|---|---|---|---|---|---|---|---|
| 2a | 0.12*) | 0.73 | 30.3 | 42.0 | 25.9 | 21400 | 4.7 | 5.5 | 0.28 | 94.9 | 2.0 | 1.4 | 90.7 |
| 2b | 0.20*) | 0.69 | 30.0 | 41.0 | 26.1 | 20100 | 4.8 | 5.5 | 0.28 | 94.3 | 2.3 | 1.8 | 88.9 |
| 2c | 0.40*) | 0.72 | 31.5 | 40.8 | 26.4 | 18100 | 4.8 | 4.5 | 0.29 | 94.2 | 2.1 | 3.0 | 85.2 |
| 2d | 0.60*) | 0.74 | 32.8 | 45.2 | 24.5 | 15200 | 4.9 | 4.8 | 0.30 | 94.5 | 1.6 | 3.7 | 83.4 |

*)% by weight based on monomer a)

Example 3

The process was performed in a concurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 3 m and a weir height of 0.25 m.

The drying gas was feed via a gas distributor (3) at the top of the spray dryer. The drying gas was partly recycled (drying gas loop) via a baghouse filter (9) and a condenser column (12). Instead of the baghouse filter (9) any other filter and/or cyclone can be used. The drying gas was nitrogen that comprises from 1% to 4% by volume of residual oxygen: Before start of polymerization the drying gas loop was filled with nitrogen until the residual oxygen was below 4% by volume. The gas velocity of the drying gas in the cylindrical part of the spray dryer (5) was 0.56 m/s. The pressure inside the spray dryer was 4 mbar below ambient pressure.

The spray dryer outlet temperature was measured at three points around the circumference at the end of the cyclindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 115° C. by adjusting the gas inlet temperature via the heat exchanger (20). The gas inlet temperature was 162° C. and the steam content of the drying gas was 0.077 kg steam per kg dry gas.

The product accumulated in the internal fluidized bed (27) until the weir height was reached. Conditioned internal fluidized bed gas having a temperature of 114 to 184° C. and a steam content of 0.077 kg steam per kg dry gas was fed to the internal fluidized bed (27) via line (25). The gas velocity of the internal fluidized bed gas in the internal fluidized bed (27) was 0.65 m/s. The residence time of the product was 45 to 300 min. The temperature of the water-absorbent polymer particles in the internal fluidized bed was 71 to 116° C.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 50° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 µm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 µm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and [2,2'-azobis[2-(2-imidazolin-2-yl)propane]dihydrochloride solution together with Bruggolite FF7 having a temperature of 5° C. was added via line (44). Each initiator was pumped in a loop and dosed via control valves to each dropletizer unit. A second filter unit having a mesh size of 140 µm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 8° C. by water in flow channels (59) as shown in FIG. 6. The dropletizer cassette (61) had 256 bores having a diameter of 170 µm and a bore separation of 15 mm. The dropletizer cassette (61) consisted of a flow channel (60) having essential no stagnant volume for homogeneous distribution of the premixed monomer and initiator solutions and one droplet plate (57). The droplet plate (57) had an angled configuration with an angle of 3°. The droplet plate (57) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.036% by weight of 3-tuply ethoxylated glycerol triacrylate, 0.0043% by weight of Bruggolite FF7, 0.270% by weight of sodiumperoxodisulfate and water. The degree of neutralization was 71%. The feed per bore was 1.6 kg/h.

The resulting water-absorbent polymer particles were analyzed. The results are summarized in Table 3.

TABLE 3

Effect of temperature and residence time in the internal fluidized bed

| Example | Temperature [° C.] | Residence Time [min] | Bulk Density [g/cm³] | CRC [g/g] | AUNL [g/g] | AUL [g/g] | Residual Monomers [ppm] | Extractables [wt. %] | Moisture [wt. %] | FSR [g/gs] | L | a | b | HC 60 |
|---|---|---|---|---|---|---|---|---|---|---|---|---|---|---|
| 3a | 71 | 45 | 0.82 | 30.9 | 35.7 | 25.3 | 25200 | 6.3 | 12.3 | 0.23 | 93.4 | 2.7 | 1.2 | 89.8 |
| 3b | 90 | 45 | 0.73 | 45.1 | 50.3 | 20.4 | 16300 | 7.2 | 8.9 | 0.21 | 93.6 | 1.2 | 2.9 | 84.9 |
| 3c | 116 | 45 | 0.68 | 48.3 | 53.4 | 16.2 | 13500 | 9.3 | 4.6 | 0.23 | 92.6 | 0.6 | 4.3 | 79.7 |
| 3d | 71 | 150 | 0.79 | 31.9 | 36.6 | 24.5 | 15000 | 4.1 | 10.2 | 0.21 | 93.4 | 2.5 | 1.7 | 88.3 |
| 3e | 90 | 150 | 0.72 | 48.0 | 53.1 | 19.2 | 13000 | 5.2 | 5.3 | 0.24 | 93.7 | 1.4 | 3.1 | 84.4 |
| 3f | 116 | 150 | 0.64 | 52.3 | 59.8 | 16.2 | 8800 | 6.1 | 1.1 | 0.26 | 94.4 | 0.2 | 4.8 | 80.0 |
| 3g | 71 | 300 | 0.75 | 45.5 | 50.2 | 23.3 | 10500 | 3.6 | 7.2 | 0.21 | 93.8 | 2.1 | 1.8 | 88.4 |
| 3h | 90 | 300 | 0.71 | 48.7 | 52.5 | 17.3 | 8100 | 4.5 | 4.4 | 0.24 | 93.6 | 1.1 | 4.8 | 79.2 |
| 3i | 115 | 300 | 0.60 | 53.3 | 58.3 | 12.2 | 7200 | 5.6 | 1.0 | 0.25 | 92.9 | 0.3 | 7.0 | 71.9 |
| 3j | 75 | 300 | 0.73 | 46.2 | 51.2 | 21.3 | 9800 | 3.6 | 6.9 | 0.21 | 93.8 | 1.9 | 1.6 | 89.0 |
| 3l | 75 | 240 | 0.72 | 45.9 | 51.8 | 18.9 | 10100 | 3.8 | 7.5 | 0.23 | 93.4 | 1.8 | 2.5 | 85.9 |
| 3k | 77 | 300 | 0.70 | 46.9 | 52.9 | 19.7 | 9300 | 3.8 | 6.2 | 0.23 | 93.7 | 1.7 | 2.0 | 87.7 |

Example 4

The process was performed in a concurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 3 m and a weir height of 0.25 m.

The drying gas was feed via a gas distributor (3) at the top of the spray dryer. The drying gas was partly recycled (drying gas loop) via a baghouse filter (9) and a condenser column (12). Instead of the baghouse filter (9) any other filter and/or cyclone can be used. The drying gas was nitrogen that comprises from 1% to 4% by volume of residual oxygen: Before start of polymerization the drying gas loop was filled with nitrogen until the residual oxygen was below 4% by volume. The gas velocity of the drying gas in the cylindrical part of the spray dryer (5) was 0.79 m/s. The pressure inside the spray dryer was 4 mbar below ambient pressure.

The spray dryer outlet temperature was measured at three points around the circumference at the end of the cyclindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 116° C. by adjusting the gas inlet temperature via the heat exchanger (20). The gas inlet temperature was 169° C. and the steam content of the drying gas was 0.058 kg steam per kg dry gas.

The product accumulated in the internal fluidized bed (27) until the weir height was reached. Conditioned internal fluidized bed gas having a temperature of 117° C. and a steam content of 0.058 to 0.225 kg steam per kg dry gas was fed to the internal fluidized bed (27) via line (25). The gas velocity of the internal fluidized bed gas in the internal fluidized bed (27) was 0.65 m/s. The residence time of the product was 150 min. The temperature of the water-absorbent polymer particles in the internal fluidized bed was 81° C.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 45° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and [2,2'-azobis[2-(2-imidazolin-2-yl)propane]dihydrochloride solution together with Bruggolite FF7 having a temperature of 5° C. was added via line (44). Each initiator was pumped in a loop and dosed via control valves to each dropletizer unit. A second filter unit having a mesh size of 140 μm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 8° C. by water in flow channels (59) as shown in FIG. 6. The dropletizer cassette (61) had 256 bores having a diameter of 170 μm and a bore separation of 15 mm. The dropletizer cassette (61) consisted of a flow channel (60) having essential no stagnant volume for homogeneous distribution of the premixed monomer and initiator solutions and one droplet plate (57). The droplet plate (57) had an angled configuration with an angle of 3°. The droplet plate (57) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.018% by weight of 3-tuply ethoxylated glycerol triacrylate, 0.036% by weight of [2,2'-azobis[2-(2-imidazolin-2-yl) propane]dihydrochloride, 0.0029% by weight of Bruggolite FF7, 0.054% by weight of sodiumperoxodisulfate and water. The degree of neutralization was 71%. The feed per bore was 1.6 kg/h.

The resulting water-absorbent polymer particles were analyzed. The results are summarized in Table 4.

TABLE 4

Effect of the steam content in the internal fluidized bed

| Example | Steam Content [kg/kg] | Bulk Density [g/cm³] | CRC [g/g] | AUNL [g/g] | AUL [g/g] | Residual Monomers [ppm] | Extractables [wt. %] | Moisture [wt. %] | FSR [g/gs] | L | a | b | HC 60 |
|---|---|---|---|---|---|---|---|---|---|---|---|---|---|
| 4a | 0.077 | 0.75 | 40.0 | 48.5 | 26.5 | 14000 | 4.2 | 5.7 | 0.27 | 96.1 | 1.0 | 2.9 | 87.4 |
| 4b | 0.172 | 0.70 | 36.6 | 44.7 | 25.1 | 9600 | 5.8 | 7.8 | 0.18 | 96.1 | 0.9 | 3.0 | 87.1 |
| 4c | 0.225 | 0.71 | 37.4 | 45.0 | 25.4 | 1400 | 2.5 | 10.7 | 0.08 | 94.2 | 2.6 | 1.7 | 89.1 |

The invention claimed is:

1. A process for producing water-absorbent polymer particles by polymerizing droplets of
   a) at least one ethylenically unsaturated monomer which bears an acid group and optionally is at least partly neutralized,
   (b) at least one crosslinker,
   $c_1$) from 0.01 to less than 0.3% by weight, based on monomer a), of at least one persulfate,
   $c_2$) at least 0.05% by weight, based on monomer a), of at least one azo initiator,
   d) optionally one or more ethylenically unsaturated monomer copolymerizable with the monomer mentioned under a),
   e) optionally one or more water-soluble polymer, and
   f) water,
   in a surrounding heated gas phase in a reaction zone and thermal posttreatment in a fluidized bed, wherein a temperature of a gas leaving the reaction zone is less than 150° C., a temperature of the water-absorbent polymer particles during the thermal posttreatment is less than 100° C., and a residence time of the water-absorbent polymer particles in the fluidized bed is from 60 to 300 minutes.

2. A process according to claim 1, wherein the heated gas phase is flowing cocurrent to the droplets through the reaction zone.

3. A process according to claim 1, wherein the monomer solution comprises from 0.05 to 0.15% by weight, based on monomer a), of the at least one persulfate.

4. A process according to claim 1, wherein the monomer solution comprises from 0.2 to 0.5% by weight, based on monomer a), of the at least one azo initiator.

5. A process according to claim 1, wherein the temperature of the gas leaving the reaction zone is from 110 to 120° C.

6. A process according to claim 1, wherein the temperature of the gas entering the reaction zone is from 160 to 200° C.

7. A process according to claim 1, wherein a gas velocity inside the reaction zone is from 0.1 to 2.5 m/s.

8. A process according to claim 1, wherein the temperature of the water-absorbent polymer particles during the thermal posttreatment is from 60 to 80° C.

9. A process according to claim 1, wherein the residence time of the water-absorbent polymer particles in the fluidized bed is from 120 to 240 minutes.

10. A process according to claim 1, wherein a gas velocity inside the fluidized bed is from 0.3 to 2.5 m/s.

11. A process according to claim 1, wherein the gas entering the fluidized bed comprises from 0.02 to 0.15 kg steam per kg of dry gas.

12. A process according to claim 1, wherein the ethylenically unsaturated monomer which bears an acid group is an ethylenically unsaturated carboxylic acid.

13. A process according to claim 1, wherein the ethylenically unsaturated monomer which bears an acid group is acrylic acid.

14. A process according to claim 1, wherein the monomer solution comprises from 0.1 to 0.15% by weight, based on monomer a) of the persulfate.

* * * * *